United States Patent
Koch et al.

(10) Patent No.: US 10,376,152 B2
(45) Date of Patent: Aug. 13, 2019

(54) MEASURING DEVICE FOR MEASURING A BODILY FUNCTION AND METHOD FOR OPERATING SUCH A MEASURING DEVICE

(71) Applicant: Drägerwerk AG & Co. KGaA, Lübeck (DE)

(72) Inventors: Jochim Koch, Ratzeburg (DE); Thomas Grassl, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 556 days.

(21) Appl. No.: 14/901,821

(22) PCT Filed: Jun. 27, 2014

(86) PCT No.: PCT/EP2014/001764
§ 371 (c)(1),
(2) Date: Dec. 29, 2015

(87) PCT Pub. No.: WO2015/000570
PCT Pub. Date: Jan. 8, 2015

(65) Prior Publication Data
US 2016/0367150 A1    Dec. 22, 2016

(30) Foreign Application Priority Data
Jul. 3, 2013 (DE) .......... 10 2013 011 141

(51) Int. Cl.
*A61B 5/00* (2006.01)
*A61B 5/01* (2006.01)
(Continued)

(52) U.S. Cl.
CPC ........... *A61B 5/01* (2013.01); *A61B 5/6843* (2013.01); *G01K 13/002* (2013.01); *G01K 15/007* (2013.01); *A61B 2562/14* (2013.01)

(58) Field of Classification Search
CPC ...... A61B 5/01; A61B 5/6843; A61B 2562/14
See application file for complete search history.

(56) References Cited

U.S. PATENT DOCUMENTS 4,331,161 A    5/1982    Patel
4,830,014 A *  5/1989    Goodman .......... A61B 5/02427
                                                600/310
(Continued)

FOREIGN PATENT DOCUMENTS

CN    1 358 075 A    7/2002
CN    102 472 670 A  5/2012
(Continued)

OTHER PUBLICATIONS

"Epidermal electronics" by Dae-Hyeong Kim et al. (Science, Aug. 12, 2011: vol. 333, No. 6244, pp. 840-843).

*Primary Examiner* — Sean P Dougherty
(74) *Attorney, Agent, or Firm* — McGlew and Tuttle, P.C.

(57) ABSTRACT

A measuring device (10) has at least one sensor (16, 18), which can be applied to the skin surface (12) of a patient for detecting a measured value with the sensor (16, 18). The device (10) has two contact surfaces (20, 22) on an underside (24), which is intended for being in contact with the skin surface (12) of the patient. A current detecting (32, 34), detects a measuring current (30) resulting from a particular effective electric resistance between the contact surfaces (20, 22). A method for operating such a measuring device (10) and a system with such a measuring device (10) are also provided.

19 Claims, 5 Drawing Sheets

(51) Int. Cl.
  *G01K 13/00* (2006.01)
  *G01K 15/00* (2006.01)

(56) References Cited

U.S. PATENT DOCUMENTS

| | | | | |
|---|---|---|---|---|
| 5,601,367 A * | 2/1997 | Nara | G01K 7/183 | 338/25 |
| 5,848,985 A * | 12/1998 | Muroki | A61N 1/205 | 604/20 |
| 5,913,830 A * | 6/1999 | Miles | A61B 5/1135 | 324/207.16 |
| 6,100,671 A * | 8/2000 | Kanesaka | H01L 35/00 | 136/204 |
| 6,526,300 B1 | 2/2003 | Kiani et al. | | |
| 6,602,201 B1 * | 8/2003 | Hepp | A61B 5/02028 | 600/526 |
| 8,075,181 B1 * | 12/2011 | Stauffer | A61B 5/015 | 374/121 |
| 9,183,738 B1 * | 11/2015 | Allen, Sr. | A61B 5/6807 | |
| 9,766,053 B1 * | 9/2017 | Okojie | G01B 7/02 | |
| 2001/0032663 A1 * | 10/2001 | Pelrine | F02G 1/043 | 136/205 |
| 2002/0026110 A1 * | 2/2002 | Parris | A61B 5/14532 | 600/347 |
| 2003/0139656 A1 | 7/2003 | Kiani et al. | | |
| 2004/0122336 A1 * | 6/2004 | Jang | A61B 5/0531 | 600/547 |
| 2004/0242976 A1 * | 12/2004 | Abreu | A61B 5/0008 | 600/315 |
| 2005/0085751 A1 | 4/2005 | Daskal et al. | | |
| 2006/0047467 A1 * | 3/2006 | Bedard | G01K 1/20 | 702/130 |
| 2006/0270942 A1 | 11/2006 | McAdams | | |
| 2006/0287608 A1 * | 12/2006 | Dellacorna | A61B 5/0488 | 600/546 |
| 2007/0206655 A1 * | 9/2007 | Haslett | A61B 5/01 | 374/141 |
| 2007/0237258 A1 * | 10/2007 | Shakeshaft | H03C 5/00 | 375/296 |
| 2007/0252714 A1 * | 11/2007 | Rondoni | A61B 5/0002 | 340/573.5 |
| 2007/0270672 A1 * | 11/2007 | Hayter | A61B 5/14514 | 600/309 |
| 2007/0289620 A1 * | 12/2007 | Stark | H01L 35/32 | 136/205 |
| 2008/0001735 A1 * | 1/2008 | Tran | G06F 19/3418 | 340/539.22 |
| 2008/0146892 A1 * | 6/2008 | LeBoeuf | G06F 19/00 | 600/300 |
| 2008/0167833 A1 * | 7/2008 | Matsen | G01N 29/14 | 702/122 |
| 2008/0300660 A1 * | 12/2008 | John | A61N 1/3785 | 607/61 |
| 2009/0015413 A1 * | 1/2009 | Gelabert | A61B 5/0031 | 340/572.1 |
| 2009/0076336 A1 * | 3/2009 | Mazar | A61B 5/0402 | 600/300 |
| 2009/0105605 A1 * | 4/2009 | Abreu | A61B 5/0008 | 600/549 |
| 2009/0163787 A1 | 6/2009 | Mannheimer et al. | | |
| 2009/0221892 A1 * | 9/2009 | Brenneman | C12Q 1/005 | 600/365 |
| 2009/0264792 A1 * | 10/2009 | Mazar | A61B 5/0531 | 600/547 |
| 2009/0287076 A1 * | 11/2009 | Boyden | A61B 5/0059 | 600/407 |
| 2009/0292195 A1 * | 11/2009 | Boyden | G06N 99/005 | 600/407 |
| 2009/0293929 A1 * | 12/2009 | Leonov | H01L 35/32 | 136/201 |
| 2009/0326611 A1 * | 12/2009 | Gillbe | A61N 1/3787 | 607/61 |
| 2010/0081892 A1 * | 4/2010 | Sethi | A61B 5/0205 | 600/301 |
| 2010/0113894 A1 * | 5/2010 | Padiy | A61B 5/0002 | 600/301 |
| 2010/0245114 A1 * | 9/2010 | Celik-Butler | G01D 11/245 | 340/8.1 |
| 2010/0253525 A1 * | 10/2010 | Engel | G08B 6/00 | 340/573.1 |
| 2010/0274447 A1 * | 10/2010 | Stumpf | G01D 1/00 | 701/36 |
| 2010/0286494 A1 * | 11/2010 | Addison | A61B 5/0059 | 600/310 |
| 2010/0292605 A1 * | 11/2010 | Grassl | G01K 1/16 | 600/549 |
| 2011/0077497 A1 * | 3/2011 | Oster | A61B 5/0002 | 600/372 |
| 2011/0133939 A1 * | 6/2011 | Ranganathan | A61B 5/0008 | 340/584 |
| 2011/0158284 A1 * | 6/2011 | Goto | A61B 5/0008 | 374/163 |
| 2011/0190615 A1 * | 8/2011 | Phillips | A61B 5/04085 | 600/372 |
| 2011/0245638 A1 * | 10/2011 | McKenna | A61B 5/02416 | 600/323 |
| 2011/0319787 A1 * | 12/2011 | Lamoise | A61B 5/103 | 600/549 |
| 2012/0078322 A1 * | 3/2012 | Dal Molin | A61B 5/0028 | 607/32 |
| 2012/0101351 A1 * | 4/2012 | Caduff | A61B 5/0507 | 600/347 |
| 2012/0106589 A1 * | 5/2012 | Ozawa | A61B 5/0008 | 374/1 |
| 2012/0109572 A1 | 5/2012 | Shimizu | | |
| 2012/0152297 A1 * | 6/2012 | Mitchell | H01L 35/30 | 136/205 |
| 2012/0245439 A1 * | 9/2012 | Andre | A61B 5/0205 | 600/310 |
| 2012/0271121 A1 * | 10/2012 | Della Torre | A61B 5/024 | 600/301 |
| 2012/0326863 A1 * | 12/2012 | Johnson | G09F 3/005 | 340/539.13 |
| 2013/0087180 A1 * | 4/2013 | Stark | H01L 35/30 | 136/205 |
| 2013/0137940 A1 * | 5/2013 | Schafer | A61B 10/0012 | 600/301 |
| 2013/0137957 A1 * | 5/2013 | Wood | A61B 5/0408 | 600/391 |
| 2013/0168336 A1 * | 7/2013 | Kim | G01L 1/146 | 211/26 |
| 2013/0201316 A1 * | 8/2013 | Binder | H04L 67/12 | 348/77 |
| 2013/0261422 A1 * | 10/2013 | Gilmore | A61B 5/0492 | 600/391 |
| 2013/0281802 A1 * | 10/2013 | Matsumoto | A61B 5/1473 | 600/309 |
| 2013/0294120 A1 * | 11/2013 | Nomura | H02M 1/36 | 363/49 |
| 2014/0091811 A1 * | 4/2014 | Potyrailo | G06K 19/0717 | 324/602 |
| 2014/0095102 A1 * | 4/2014 | Potyrailo | G01R 27/28 | 702/127 |
| 2014/0100432 A1 * | 4/2014 | Golda | A61B 5/04325 | 600/301 |
| 2014/0200486 A1 * | 7/2014 | Bechtel | A61B 5/14551 | 600/592 |
| 2014/0347491 A1 * | 11/2014 | Connor | A61B 5/1114 | 348/158 |
| 2015/0126834 A1 * | 5/2015 | Wang | A61B 5/6833 | 600/345 |
| 2016/0336501 A1 * | 11/2016 | Kasichainula | H01L 35/32 | |
| 2017/0030952 A1 * | 2/2017 | Shamir | G01R 21/14 | |
| 2017/0258386 A1 * | 9/2017 | Woltjer | A61B 5/204 | |
| 2017/0265769 A1 * | 9/2017 | Quinlan | A61B 5/1123 | |
| 2017/0265770 A1 * | 9/2017 | Quinlan | A61B 5/1123 | |

(56) References Cited

U.S. PATENT DOCUMENTS

FOREIGN PATENT DOCUMENTS

| | | |
|---|---|---|
| DE | 696 04 767 T2 | 2/2000 |
| DE | 100 05 526 A1 | 8/2001 |
| DE | 694 31 281 T2 | 5/2003 |
| DE | 10 2004 031 672 A1 | 1/2006 |
| DE | 10 2005 037921 B3 | 6/2006 |
| GB | 2 061 496 A | 5/1981 |

\* cited by examiner

MEASURING DEVICE FOR MEASURING A BODILY FUNCTION AND METHOD FOR OPERATING SUCH A MEASURING DEVICE

CROSS REFERENCE TO RELATED APPLICATIONS

This application is a United States National Phase Application of International Application PCT/EP2014/001764 filed Jun. 27, 2014 and claims the benefit of priority under 35 U.S.C. § 119 of German Patent Application 10 2013 011 141.2 filed Jul. 3, 2013 the entire contents of which are incorporated herein by reference.

FIELD OF THE INVENTION

The present invention pertains to a measuring device for measuring a bodily function by means of at least one sensor, which is indirectly or directly in contact with the skin of a human being or a patient, and to a method for operating such a measuring device. The measurement of the bodily function pertains, for example, to a body temperature of the patient in this context.

BACKGROUND OF THE INVENTION

Such measuring devices, especially such measuring devices in the form of a temperature-measuring device, are known per se, for example, from DE 10 2005 037 921 B3. It is, however, problematic in case of measuring devices which are intended to be placed on the skin surface of the patient that the measuring device in question may become detached and a reliable measurement of the bodily function is thus no longer possible. Situations in which the measuring device is still located on the skin surface but it no longer has a sufficient contact with the skin surface for a reliable measurement result have proved to be especially problematic in this connection. The measurement of a body temperature of a newborn in an incubator may be mentioned as an example in this context, because the internal temperature of the incubator is regulated in relation to the measured body temperature. When a temperature-measuring device intended for this is still located on the skin surface of the newborn, it cannot be recognized based on the simple optical appearance whether the measured values supplied by the temperature-measuring device are reliable. When the temperature-measuring device has, in fact, already become partially detached from the skin surface, the internal temperature of the incubator is, for example, needlessly raised due to the temperature regulation based on a now erroneous measured value. This scenario is expressly an exemplary scenario only, and other examples can be created with other bodily functions monitored by a measuring device, and these examples which likewise illustrate that it is especially important to recognize whether the particular measured values supplied are reliable, consequently, whether the measuring device is still in contact with the skin surface of the patient to such an extent that reliable measurement results can be expected.

The above-mentioned DE 10 2005 037 921 B3 already pertains to this problem and proposes a possibility for how an insufficient skin contact of the measuring device can be detected.

SUMMARY OF THE INVENTION

An object of the present invention is to provide another embodiment of a measuring device of the above-mentioned type and a method for operating same, which respective device and method make it possible to detect an insufficient skin contact of the measuring device and thus increase the reliability of the particular measured value detected and/or the safety of the patient.

This object is accomplished by a measuring device according to the present invention. Such a measuring device, which has at least one sensor and which can be arranged on the skin surface of a patient for detecting a measured value by means of the sensor, comprises for this at least one first and at least one second contact surface on an underside of the measuring device, which underside is intended for being contacted with the skin surface of the patient, as well as a detecting means for detecting a measuring current resulting from a respective effective electric resistance (prevailing/active electric resistance) between the at least one first and second contact surfaces. The detected measuring current is an indicator of an electric resistance or an electric conductivity between the at least one first and second contact surfaces, hereinafter called briefly first and second contact surfaces and together "the contact surfaces" or "both contact surfaces" for linguistic simplicity.

The measuring current resulting from a current flow between the contact surfaces or a signal that can be generated on this basis will hereinafter also be called contact signal, since a measuring current can only flow if the measuring device still has sufficient contact with the skin surface of the patient. A measuring current from the sensor comprised by the measuring device or a signal that can be generated on this basis will hereinafter be called sensor signal for distinction.

Provisions are made in a method for operating such a measuring device for a measuring current resulting from a particular effective electric resistance between the at least one first and second contact surfaces to be detected and for this measuring current to be analyzed as a contact signal or for a contact signal to be generated on the basis of the measuring current.

One advantage of the present invention is that it is immediately and unambiguously certain based on the contact signal whether the measuring device is still sufficiently in contact with the skin.

This is based on the fact that the electric resistance between the two contact surfaces increases greatly when the measuring device becomes detached from the skin surface. When one of the contact surfaces is no longer in contact with the skin surface, such a high resistance will develop that no measuring current can flow any longer and the contact signal will disappear.

Any skin contact that is thus detected as being insufficient represents an error situation in relation to the monitoring of the bodily function in question, and such an error situation can be displayed to the patient and/or to the medical staff in order for suitable countermeasures to be able to be taken, especially to place the measuring device again correctly. In addition or as an alternative, such an error situation may also be signaled to a medical device, to which the measuring device is connected, in order for the error situation to be able to be displayed to the patient and/or to the medical staff by means of the medical device and in order for suitable countermeasures to be able to be taken.

The resistance or a conductivity or, as an indicator of the resistance, the value of a current flowing between the contact surfaces, can be measured. Any circuit or device suitable for this is and will hereinafter generally be called detecting means for detecting the measuring current, an electric resistance or an electric conductivity between the two contact surfaces. Such a circuit is correspondingly also a signaling means for generating the contact signal. One example of a circuit that can be considered in this respect is an analysis circuit with a so-called Darlington circuit, which is known per se.

Provisions are made in one embodiment of the measuring device for the measuring device to also comprise, in addition to the sensor already mentioned, another sensor of the same kind, i.e., for example, a first temperature sensor and a second temperature sensor, a first pressure sensor and a second pressure sensor, etc. The body temperature of the patient and a temperature close to the ambient temperature can be detected simultaneously in case of such a measuring device, which comprises, for example, two temperature sensors. For example, the body temperature can now be considered in relation to the ambient temperature. For the sake of linguistic simplicity, the sensor or each sensor individually and together will hereinafter be called sensor system for short.

An enlarged global area of the contact surfaces and above all a local distribution of the contact surfaces on the underside of the measuring device are obtained when the contact surfaces are arranged in the measuring device in the form of a grid or in a labyrinthine pattern on the underside of the measuring device. Due to this local distribution, a loss of contact of the measuring device with the skin surface in the area of, e.g., a corner of the measuring device is not rated as an error situation, because reliable determination of a measured value in respect to the particular bodily function being monitored may still be possible in case of such a loss of contact. Such a configuration and arrangement of the contact surfaces consequently advantageously avoids unnecessary false alarms. In addition to such a grid-like or labyrinthine arrangement, for example, a comb-like arrangement may be considered, in which the two comb surfaces mesh with one another. Such an arrangement or any arrangement having a similar effect shall be covered by the term "labyrinthine" for the explanation of the description being presented here.

If the measuring device itself comprises a display device that can be actuated as a function of the particular contact signal generated, the particular measuring device in which there is an insufficient contact with the skin surface of the patient can be immediately recognized when such a display device is activated. The term display device is defined predominantly as optical display devices, i.e., for example, an LED or the like. It shall nevertheless apply to the explanation of the term that it also covers devices that can also signal such an insufficient contact with the skin on an acoustic basis and thus likewise act as a display device. One example of such an display device is an electric buzzer.

Provisions are made in a special embodiment of the measuring device described here and below for said measuring device to have a local power source for power supply at least for the display device or an Application-Specific Integrated Circuit (ASIC) or the like with at least one display device. A capacitor and/or a thermocouple or a Peltier element may be considered for use as a local power source. A capacitor acting as a local power source may be charged in connection with the electric power supply (energization) of the measuring device. A local temperature difference, for example, a difference between a temperature on the skin surface and an ambient temperature, may be used for charging the local power source and hence for the power supply of the ASIC, etc., by means of a thermocouple or a Peltier element.

Provisions are made in another special embodiment of the measuring device described here and below for said measuring device to comprise an adhesive layer, which is suitable for bringing about the adhesion of the measuring device on the skin surface of the patient on the basis of van der Waals forces on an underside intended for contact with the skin surface of the patient, and for the contact surfaces to be embedded in or to be applied to said adhesive layer on a surface of the adhesive layer, which said surface is intended for contact with the skin surface of the patient. Such an adhesive layer with contacts embedded in it can be manufactured now in the form of a thin film. Further details of such a film can be found, for example, in the technical article "Epidermal electronics" by Dae-Hyeong Kim et al. (Science, 12, August 2011: Vol. 333, No. 6244, pp. 840-843).

If the sensor system and the two contact surfaces are connected electrically in parallel and a power cut-off element, for example, a diode, is located either in a current path to the sensor system or in a current path to the contact surfaces, energization and generation and analysis of the contact signal and of the sensor signal are possible with a simple two-wire feed line. This makes the measuring device especially inexpensive by avoiding, for example, a more than two-wire feed line that would otherwise be necessary. Provisions are made in this connection for the measuring device to be able to be energized in a timed manner with alternating polarity to generate a measuring current and to be energized in this manner during operation. If the power cut-off element is located, for example, in the current path to the contact surfaces, the following situation arises: The current being fed flows during a first clock phase, for example, to both the sensor system and the contact surfaces. During a second, complementary clock phase, the current being fed flows, because of the power cut-off element that now becomes active corresponding to the polarity, to the sensor system only. Consequently, the contact signal as well as the sensor signal and a corresponding measuring current are generated during the first clock phase. Due to the parallel connection, the two signals are present at the output of the measuring device in the form of a sum signal. Only a sensor signal is obtained from the sensor signal during the second clock phase. A simple pole reversal of the current being fed is thus sufficient for supplying, for example, the sensor system and the contact surfaces in case of a first polarity and to supply the sensor system only in case of a second, reversed polarity. The sum signal supplied during the first clock phases (contact signal plus sensor signal) can thus be unambiguously distinguished from the sensor signal supplied during the second clock phases during an analysis of the measuring current returned from the measuring device corresponding to the timing of the fed current. A possible detachment of the measuring device from the skin surface of the patient can also be recognized from the sum signal, because if the sum signal drops below a preset threshold value, this can be interpreted as detachment of the measuring device. The threshold value is set for this on the basis of the contribution the analysis circuit is normally expected to make to the sum signal, so that, for example, a value slightly below such a normally expected value is selected.

On the whole, the present invention is also a system with a medical device and with at least one measuring device of the type being described here and below, which is connected to the medical device by means of a first feed line and by means of a second feed line. A feed current can be fed to the measuring device by means of the medical device in the above-described manner alternatingly via the first feed line and the second feed line, and the feed current is fed to the measuring device in this manner by means of the medical device during the operation of the system. The measuring current and hence the contact signal and the sensor signal can be fed to the medical device through the measuring device via a respective complementary feed line, and the measuring current is fed to the medical device through the measuring device during the operation of the system. When the feed current is fed to the measuring device via the first feed line, the complementary feed line, via which the measuring current is fed to the medical device, is the second feed line, and vice versa. The measuring current can be analyzed by means of the medical device and is analyzed by the medical device during the operation of the system. Such an analysis comprises, for example, the fact that an optical or acoustic display device is actuated by the medical device on the basis of the contact signal.

An exemplary embodiment of the present invention will be explained in more detail below on the basis of the drawings. Mutually corresponding objects or elements are designated by the same reference numbers in all figures.

The exemplary embodiment or each exemplary embodiment shall not be interpreted as representing a limitation of the present invention. Rather, variations and modifications are possible within the framework of the present disclosure, especially such variants and combinations that the person skilled in the art can find with a view to accomplish the object, for example, by combining or varying individual features that are described in the general or special part of the description and are contained in the claims and/or in the drawings and lead to a new subject due to features that can be combined. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
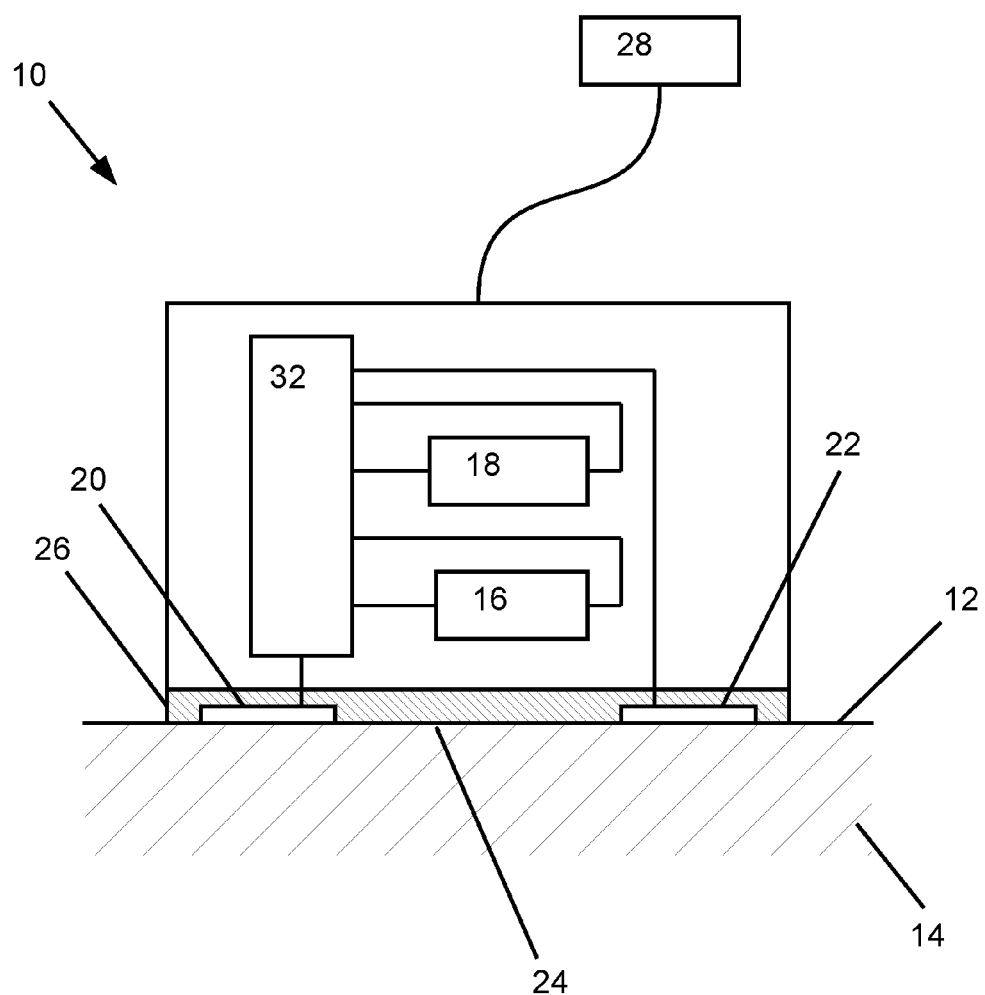
FIG. 1 is a schematic view of a measuring device, which is arranged on the skin surface of the patient, for measuring a bodily function of a patient.

FIG. 1 shows a schematically simplified view of a measuring device 10, which can be placed on the surface (skin surface 12) of the skin 14 of a human being or patient for measuring a bodily function of a human being or patient and is placed thereon during use. The measuring device 10 comprises a first sensor 16 and, in the embodiment being shown, an optional second sensor 18 (individually or together also called sensor system), as well as at least one first contact surface 20 and at least one second contact surface 22 on an underside 24 of the measuring device 10, which said underside is intended for contact with the skin surface 12. Each sensor 16, 18 may be arranged within the measuring device 10 such that the sensor system is located on the underside 24 of the measuring device 10 and is itself directly in contact with the skin surface 12. A sensor 16, 18, which is located in the interior of the measuring device 10, is in contact with the skin surface 12 at least still indirectly via the surrounding measuring device 10.

As was already defined in the introduction, the at least one first contact surface 20 and the at least one second contact surface 22 are called the first contact surface and second contact surface and together "the contact surfaces" or "both contact surfaces" for the sake of linguistic simplicity. The term patient will also be used throughout below instead of the expression human beings or patients, likewise for the sake of linguistic simplicity. However, this shall be defined broadly, so that persons who are not under medical care are also covered, because the principle being described here and below may also be considered, for example, in connection with the measurement of a bodily function of an athlete or the like.

In the embodiment of the measuring device 10 shown in FIG. 1, the contact surfaces 20, 22 are embedded in or placed on an optional adhesive layer 26 in the form of a thin film. This adhesive layer 26 is located on an underside 24 of the measuring device 10, which said underside is intended for contact with the skin surface 12 of the patient. The film acts as an adhesive layer 26, because it is suitable based on its material properties and surface structure for bringing about the adhesion of the measuring device 10 on the skin surface 12 of the patient on the basis of van der Waals forces. The film/adhesive layer 26 is enclosed by the measuring device 10 as an integral component. Without such an adhesive layer 26, the contact surfaces 20, 22 are located on the underside 24 of the measuring device 10, which underside is now obtained, and, for example, an adhesive or a hydrogel is applied to the underside 24 for adhesion of the measuring device 10. Such an applied adhesive layer is not part of the measuring device 10, contrary to the film acting as an adhesive layer 26, and is applied only when needed.

The measuring device 10 can be connected to a medical device 28, which is not shown in more detail and is usually called monitor in technical terminology, and is connected to such a medical device 28 during use. The measuring device 10 comprises a detecting means for detecting a measuring current 30 (FIG. 2) resulting because of a particular effective electric resistance between the contact surfaces 20, 22 or for detecting an electric resistance or an electric conductivity between the contact surfaces 20, 22.

An electronic unit 32 is shown in a schematically simplified manner in the view shown in FIG. 1 as the detecting means for detecting the particular measuring current 30, electric resistance or an electric conductivity. The electronic unit 32 comprises, for example, an analysis circuit 34 with a so-called Darlington circuit 36, which is known per se, as it is shown in FIG. 2.

Based on such an analysis circuit 34 comprising such a Darlington circuit 36, but without abandoning a continued general validity, it will be explained below how the detection of an insufficient skin contact and hence an increase in the reliability of the measured values detected with the sensor system 16, 18 and/or an improvement of the patient's safety can be achieved with the measuring device 10 provided according to the invention.

Figure 2:
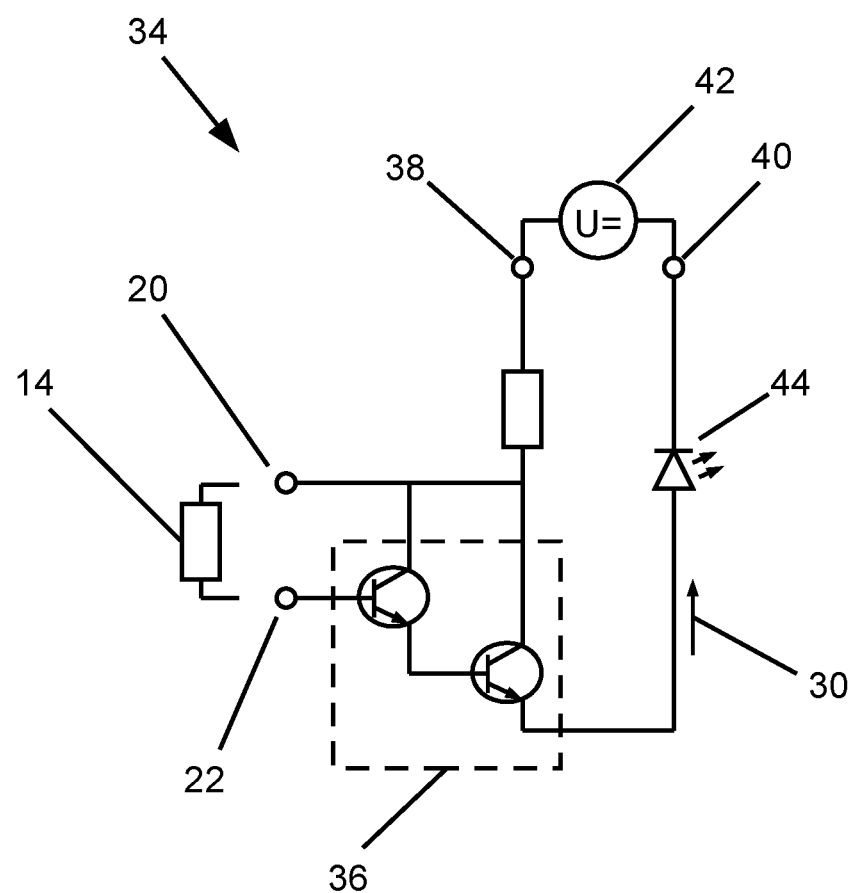
FIG. 2 is a circuit diagram of a possible embodiment of an analysis circuit for detecting whether the measuring device still has sufficient contact with the skin surface of the patient.

The two contact surfaces 20, 22 of the measuring device 10 are shown in FIG. 2 as contact points in the sense of a simple view. The resistance shown by these contact points corresponds to the skin 14 and to the skin surface 12 of the patient in question. Besides the two contact surfaces 20, 22 acting as outputs of the analysis circuit 34, this analysis circuit 34 comprises two contact points acting as inputs 38, 40. An external d.c. power source 42 can be connected in this case. This is suitable for driving the measuring current 30 via the analysis circuit 34. However, the measuring current 30 can flow in the analysis circuit 34 only when there is an electrically conductive contact between the contact surfaces 20 22. Such a contact can be established via the skin 14 and the skin surface 12 of the patient. It is necessary for this that both contact surfaces 20, 22 lie on the skin surface 12. It is in this case only that an electric current (a rather weak electric current based on the comparatively high electric resistance), which will be amplified with the Darlington circuit 36—or another suitable amplifying circuit—to such an extent that, for example, an optional display device 44, which is shown here in the form of an LED, can be caused to light, will flow between the contact surfaces 20, 22. An active, lighting display device 44 consequently indicates a contact of the contact surfaces 20, 22 with the skin surface 12 of the patient. An inactive display device 44 correspondingly shows an interrupted or insufficient contact of the contact surfaces 20 22 with the skin surface 12.

Thus, the particular measuring current 30 shows whether the measuring device 10 is still in contact with the skin surface 12 of the patient and is correspondingly also called contact signal. A measuring current supplied by the sensor system 16, 18 (FIG. 1) is called sensor signal for distinction.

Due to the electronic unit 32 of the measuring device 10 comprising such an analysis circuit 34 or a similarly acting analysis circuit, it is consequently possible to detect an insufficient skin contact and to generate a corresponding contact signal. Based on such a possibility of detection, it is also possible to increase the reliability of the particular measured values detected with the measuring device 10 and the sensor system 16, 18 thereof and/or to improve the safety of the patient.

This happens especially when treatment measures, which are brought about automatically by a particular medical device 28, to which the measuring device 10 is connected, depend on the detected measured values. Such a medical device 28 is, for example, an incubator for newborns, which brings about, as a treatment measure, a regulation of the ambient temperature for the newborn, i.e., a regulation of an internal temperature of the incubator, as a function of the body temperature of the newborn. If the measured temperature value of the measuring device 10 is no longer reliable (based on the sensor signal) during the detection of the body temperature by means of a measuring device 10, because the measuring device 10 is no longer sufficiently in contact with the skin surface 12 of the newborn, the temperature regulation must not be performed on the basis of a measured value still being generated any longer. The error situation now occurring must be signaled in a suitable manner. This may happen by means of a display device 44. The contact signal, the measuring current 30, or an absence of measuring current 30 may, however, also be analyzed automatically, in addition or as an alternative, so that a medical device 28 or the like, for example, an incubator, which is arranged downstream, is brought into a presettable or preset state and/or the medical device 28 sends an optical and/or acoustic alarm signal.

Figure 3:
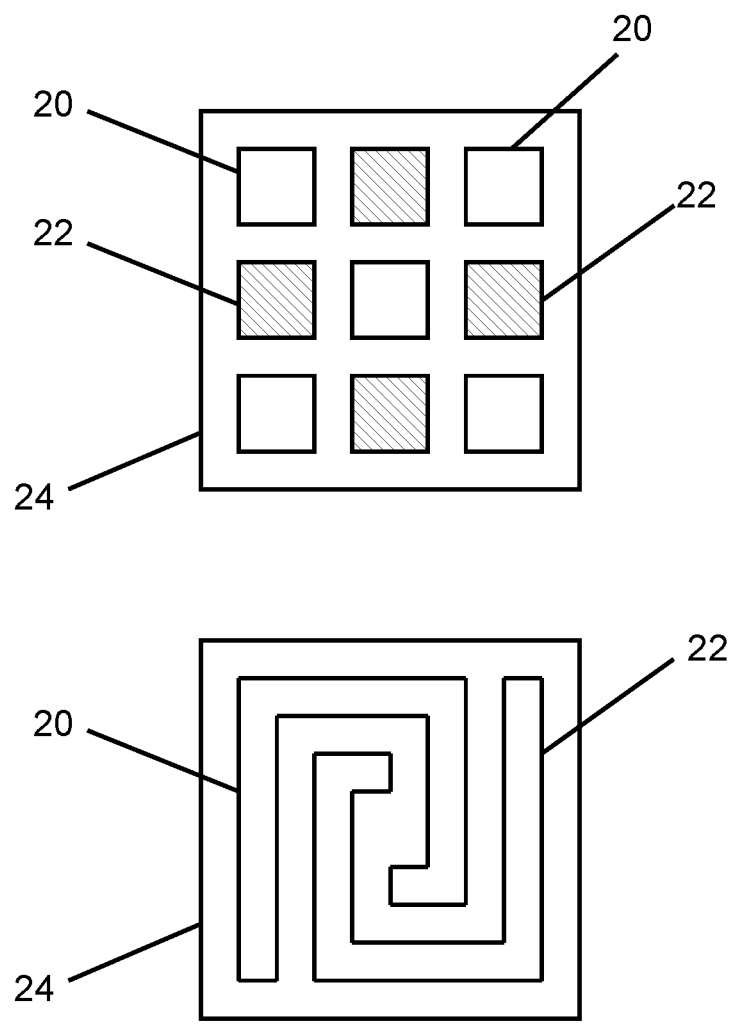
FIG. 3 is a schematic view of possible embodiments of contact surfaces formed or arranged on an underside of the measuring device.

The view in FIG. 3 shows two possible embodiments of an underside 24 of the measuring device 10. An arrangement of the contact surfaces 20, 22 in the form of a grid is shown in the upper area of the view shown in FIG. 3. It is seen here that the measuring device 10 may also comprise a plurality of first and second contact surfaces 20, 22. The second contact surfaces 22 are marked by shading in the upper area of the view for distinction from the first contact surfaces 20. A simple labyrinth-like arrangement of the contact surfaces 20, 22 is shown in the lower area of the view shown in FIG. 3.

The peculiarity of such an arrangement or of a similar arrangement and/or distribution of the contact surfaces 20, 22 is that when, for example, the first contact surface 20 shown on top on the left side in the grid-like arrangement of the contact surfaces 20, 22, the current can still flow from one of the other first contact surfaces 20 via the skin 14 and the skin surface 12 to the second contact surfaces 22. An only punctiform detachment of the measuring device 10 from the skin surface 12, in which case reliable measured values can still be obtained from the sensor system 16, 18 in question, does not consequently have to be rated as an error situation. If, by contrast, the measuring device 10 has exactly one first and exactly one second contact surface 20, 22 with respective small spatial dimensions, as this can readily be provided in case of an especially simple measuring device 10 or a measuring device 10 that is especially sensitive with respect to the detection of a detachment from the skin surface 12, any lifting off of either the exactly one first or exactly one second contact surface 20, 22 leads to an interruption of the measuring current 30 and hence to an automatically detectable error situation, which can be signaled.

Figure 4:
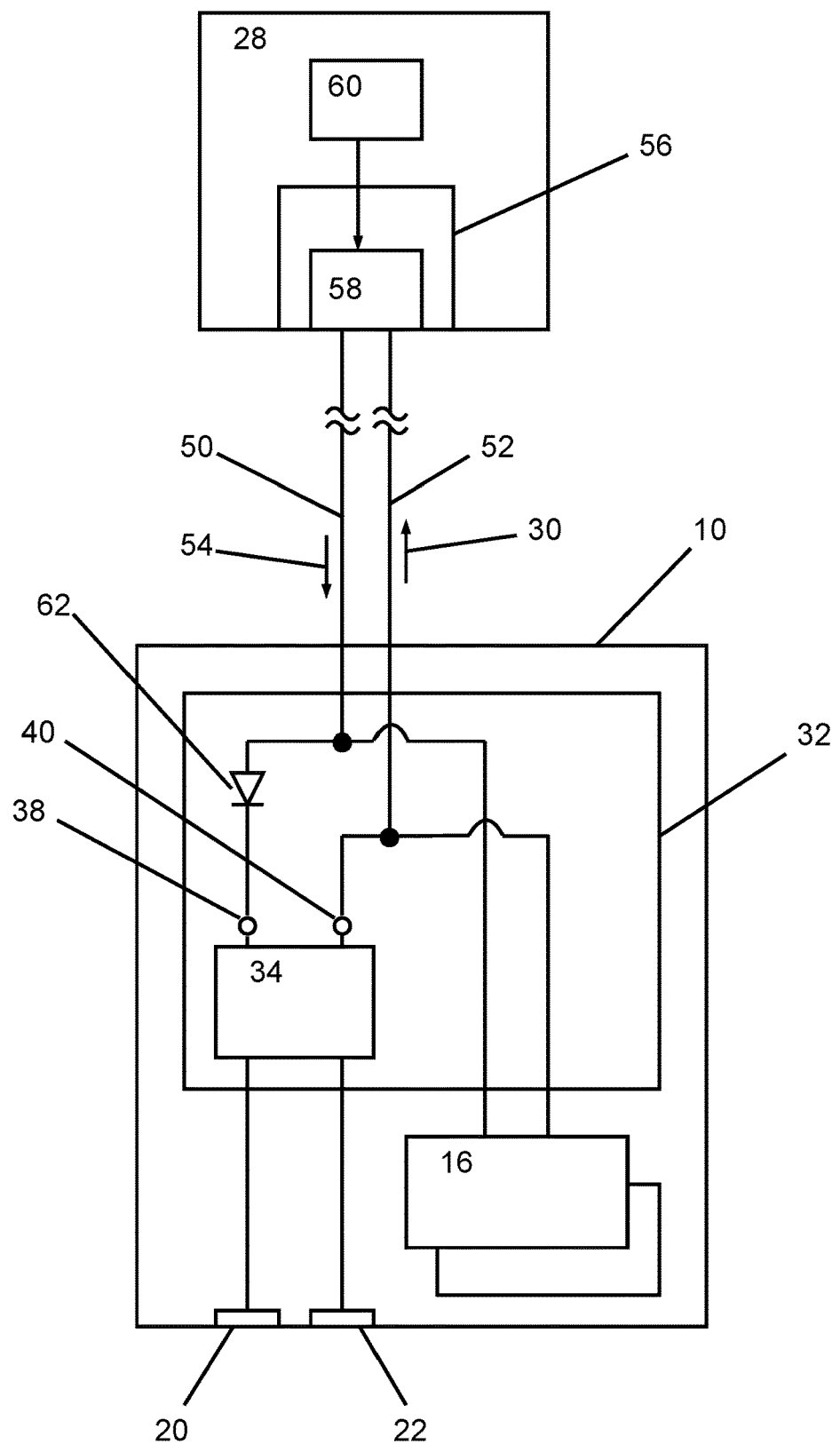
FIG. 4 is a schematic view of a measuring device according to FIG. 1 with further details.

FIG. 4 shows a schematically simplified view of the measuring device 10 from FIG. 1, wherein the analysis circuit 34 according to FIG. 2 (or an analysis circuit with a comparable functionality) is shown as being comprised by the electronic unit 32. To generate a particular measuring current 30, feed current is fed to the measuring device 10 and to the electronic unit 32 thereof from a medical device 28 via feed lines 50, 52, of which there are exactly two in this case. The sensor system 16, 18 and the contact surfaces 20, 22—in this case the sensor system 16, 18 on one side and the contact surfaces 20, 22 together with their analysis circuit 34 on the other side—are connected electrically in parallel within the measuring device 10, so that the feed current 54 reaches, in principle, the sensor system 16, 18 and the analysis circuit 34.

A plurality of the measuring devices 10 being described here or other measuring devices can usually be connected to the medical device 28. A measuring device 10 is connected to an input channel 56 of the medical device 28. The medical device 28 comprises, as a component of a circuit of such an input channel 56, a pole reversal circuit 58, which is known per se and is not therefore shown in more detail and which is actuated by the medical device 28 in a timed manner by means of a clock generator 60. As a result, the feed current 54 is fed to the measuring device 10 via the first feed line 50 while the pole reversal circuit 58 is in a first switching position and via the second feed line 52 while the pole reversal circuit 58 is in a complementary second switching position. In order for a differentiation by the measuring device 10 to be possible, a power cut-off element 62, i.e., for example, a diode 62, is provided either in the current path to the contact surfaces 20, 22 or in the current path to the sensor system 16, 18. The diode 62 shown in FIG. 4 causes a feed current 54 being fed via the first feed line 50 to reach the analysis circuit 34 and the contact surfaces 20, 22, on the one hand, and the sensor system 16, 18, on the other hand. The resulting measuring current 30 flowing back to the medical device 28 consequently corresponds to the sum of the measuring currents 30 generated by the analysis circuit 34 and the sensor system 16, 18. The measuring current 30 flowing back to the medical device 28 is consequently a sum signal from the analysis circuit 34 and the sensor system 16, 18. The diode 62 is switched into the cut-off direction for a feed current 54 fed via the second feed line 52 (after a pole reversal by the medical device 28), so that the resulting measuring current 30 flowing back to the medical device 28 depends only on the sensor system 16, 18 and the measuring current generated there.

The contribution of the analysis circuit 34 to the sum signal is known (for example, on the basis of a maximum current amplification occurring there), so that the measuring current 30 on which the sum signal is based can be compared to a preset threshold value in order to determine whether the measuring device 10 still has sufficient contact with the skin surface 12. When such a contact is no longer present and the sum signal does not consequently contain any contribution of the contact signal, the measuring current 30 is below a suitably selected threshold value. The threshold value is selected for this on the basis of the contribution the contact signal is normally expected to make to the sum signal, for example, in the form of a value reduced by 5%, 10% or the like.

The measured value recorded by the measuring device 10 with the sensor system 16, 18 present there can be analyzed directly in the corresponding clock phases on the basis of the particular measuring current 30 that is returned. The possibility can be considered for this that a digital value, which can be processed by means of an electronic unit (not shown) of the medical device 28, and which can be displayed, for example, on a display screen or the like of the medical device 28 and/or can be logged in a memory of the medical device 28, is formed by the medical device 28 on the basis of the measuring current 30 with a digital/analog converter.

In a special embodiment of the measuring device 10, not shown, a power cut-off element 62 each, i.e., for example, a diode 62 each, is located both in the current path to the contact surfaces 20, 22 and in the current path to the sensor system 16, 18, it being located either following the first feed line 50 with antiparallel cut-off directions or each following the first feed line 50 and the second feed line 52 with parallel cut-off directions. Now, in case of a timed alternating energization of the measuring device 10, only either the sensor signal or the contact signal is generated during each clock phase, and the measuring current 30 returned is directly an indicator of the particular signal.

Figure 5:
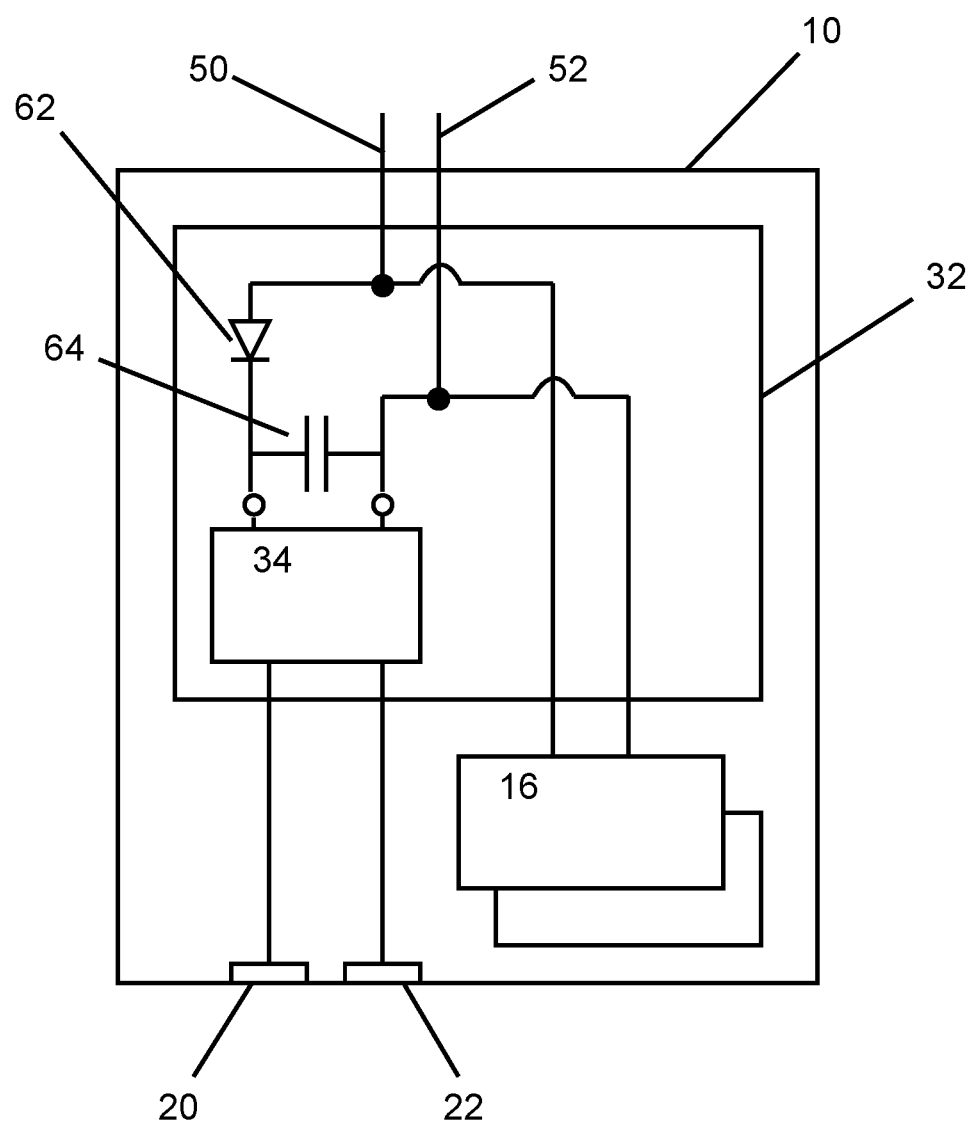
FIG. 5 is a measuring device according to FIG. 1 and FIG. 4 with an optional local power source.

The view shown in FIG. 5 shows further, but optional details of the measuring device 10. The measuring device 10 thus comprises a local power source 64, for example, in the form of a capacitor 64 or the like. The capacitor 64 is charged by means of the feed current 54. In case of a timed energization of the measuring device 10, the capacitor 64 acts like the d.c. power source 42 shown in FIG. 2 and makes possible, for example, the power supply of a display device 44 even for the short time periods of the timed energization, during which the diode 62 cuts off the feed current 54. A thermocouple or a Peltier element (PT element) (not shown) may be considered as an additional or alternative possibility of embodying a local power source 64. A temperature difference between a temperature on the skin surface 12 of the patient and an ambient temperature, which can usually be assumed to occur, can be used in case of such a local power source 64 to feed the analysis circuit 34 and to supply the display device 44 with power.

The analysis circuit 34 shown in FIG. 2 is only one possibility of embodying the detecting means for detecting a measuring current 30 resulting from a particular effective electric resistance between the two contact surfaces 20, 22. The analysis circuit 34 being shown represents an especially simple embodiment possibility. Such detecting means for detecting a particular resulting measuring current 30 may just as well be embodied in the form of an ASIC or the like (not shown). It is possible now, for example, to actuate a display device 44 in the form of an LED or the like or of a plurality of LEDs, which displays the particular status of the contact signal by a change in color or alternating activation of exactly one display device 44 to the patient and/or the medical staff Such an ASIC or the like can be supplied with a sufficient quantity of electric power with the feed current 54 and otherwise at least briefly from a local power source 64, as was described above, since ASICs or other forms of integrated semiconductor circuits are known to have only a very low power consumption.

Individual prominent aspects of the description can thus be briefly summarized as follows: Provided are a measuring device 10 with at least one sensor 16, 18, which can be placed on the skin surface 12 of a patient for detecting a measured value by means of the sensor 16, 18 and is characterized in that it has two contact surfaces 20, 22 on an underside 24, which is intended for being in contact with the skin surface 12 of the patient, as well as a detecting means 32, 34 for detecting a measuring current 30 resulting from a particular effective electric resistance between the contact surfaces 20, 22, as well as a method for operating such a measuring device 10 and a system having such a measuring device 10.

While specific embodiments of the invention have been shown and described in detail to illustrate the application of the principles of the invention, it will be understood that the invention may be embodied otherwise without departing from such principles.

The invention claimed is:
1. A measuring device comprising:
at least one sensor, wherein the measuring device is positionable on skin surface of a patient for the at least one sensor to detect a measured value;
at least one first contact surface on an underside of the measuring device;
at least one second contact surface on the underside of the measuring device, which said underside is intended for being in electrical contact with the skin surface of the patient, the at least one first contact surface and the at least one second contact surface being arranged to have a resistance between the at least one first contact surface and the at least one second contact surface that is a function of electrical contact of the at least one first contact surface and the at least one second contact surface with the skin surface of the patient;
a detecting means for detecting a measuring current resulting from a particular effective electric resistance between the at least one first contact surface and second contact surface, wherein the detected measuring current is a function of electrical contact of the at least one first contact surface and the at least one second contact surface with the skin, wherein the sensor and the at least one first and second contact surfaces are connected electrically in parallel and wherein a power cut-off element is located either in a current path to the sensor or in a current path to the at least one first and second contact surfaces; and a feed circuit to feed current to the measuring device alternatingly via a first feed line and a second feed line, the sensor and the at least one first and second contact surfaces being connected electrically in parallel to the first feed line and a second feed line and the measuring current comprises a sum signal comprising a contact signal, which is a function of electrical contact of the at least one first contact surface and the at least one second contact surface with the skin and a sensor signal provided by the sensor.

2. A measuring device in accordance with claim 1, further comprising another sensor of a same type as the at least one sensor and in addition to the at least one sensor.

3. A measuring device in accordance with claim 1, wherein the contact surfaces are arranged in the form of a grid or in a labyrinthine pattern on the underside of the measuring device.

4. A measuring device in accordance with claim 1, further comprising a display device, which is actuated as a function of the detected measuring current corresponding to the particular effective electric resistance or a particular effective electric conductivity between the at least one first and second contact surfaces.

5. A measuring device in accordance with claim 4, further comprising a local power source for supplying at least the display device with power.

6. A measuring device in accordance with claim 1, further comprising an adhesive layer on or forming the underside of the measuring device, which said underside is intended for being in contact with the skin surface of the patient, said adhesive layer being suitable for bringing about an adhesion of the measuring device on the skin surface of the patient based on van der Waals forces, wherein the at least one first and second contact surfaces are embedded in or placed on a surface of the adhesive layer, which said surface is intended for being in contact with the skin surface of the patient.

7. A measuring device in accordance with claim 1, wherein the sensor is a temperature sensor and the measuring device comprises a temperature-measuring device.

8. A measuring device in accordance with claim 1, further comprising a local power source, wherein the feed current is used to charge the power source.

9. A measuring device in accordance with claim 1, further comprising an electrothermal converter and a local power source, wherein a temperature difference occurring in an area of the measuring device is used to charge the power source by means of the electrothermal converter.

10. A system comprising:
a medical device; and
at least one measuring device connected to the medical device by means of a first feed line and a second feed line, the measuring device comprising:
at least one sensor connected to the first feed line and the second feed line, wherein the measuring device is positionable on skin surface of a patient for the at least one sensor to detect a measured value and provide a sensor signal;
at least one first contact surface connected to the first feed line and the second feed line, the at least one first contact surface being provided on an underside of the measuring device;
at least one second contact surface connected to the first feed line and the second feed line, the at least one second contact surface being provided on the underside of the measuring device, which said underside is intended for being in electrical contact with the skin surface of the patient, the at least one first contact surface and the at least one second contact surface being arranged to have a resistance between the at least one first contact surface and the at least one second contact surface that is a function of electrical contact with the skin; and
a detecting means for detecting a measuring current resulting from a particular effective electric resistance between the at least one first contact surface and second contact surface, the detected measuring current comprises the contact signal that is a function of electrical contact of the at least one first contact surface and the at least one second contact surface with the skin, wherein a feed current is fed to the measuring device, by means of the medical device, alternatingly via the first and second feed lines, and the measuring current comprises a sum signal comprised of the contact signal and the sensor signal, which sum signal can be analyzed by means of the medical device during operation, which sum signal is fed to the medical device by the measuring device via a respective complementary feed line.

11. A system in accordance with claim 10, further comprising another sensor, wherein each sensor is a temperature sensor and the measuring device comprises a temperature-measuring device.

12. A system in accordance with claim 11, wherein the contact surfaces are arranged in the form of a grid or in a labyrinthine pattern on the underside of the measuring device.

13. A system in accordance with claim 11, wherein the measuring device further comprises:
a display device, which is actuated as a function of the detected electric resistance or the detected electric conductivity between the at least one first and second contact surfaces; and
a local power source for supplying at least the display device with power.

14. A system in accordance with claim 11, wherein the measuring device further comprises:
an adhesive layer defining the underside for contact with the skin surface of the patient, said adhesive layer providing an adhesion of the measuring device on the skin surface of the patient based on van der Waals forces, wherein the at least one first and second contact surfaces are embedded in or placed on a surface of the adhesive layer to from a portion of the underside for contact with the skin surface of the patient.

15. A system in accordance with claim 11, wherein the measuring device further comprises a power cut-off element and each sensor and the at least one first and second contact surfaces are connected electrically in parallel and wherein the power cut-off element is located either in a current path to each sensor or in a current path to the at least one first and second contact surfaces.

16. A system in accordance with claim 10, wherein:
the sensor and the at least one first and second contact surfaces are connected to the first feed line and the second feed line electrically in parallel; and
a power cut-off element, is located either in a current path to the sensor or in a current path to the at least one first and second contact surfaces.

17. A system in accordance with claim 16, wherein:
the feed circuit feeds current to the measuring device alternatingly to feed the first feed line and the second feed line with current during a first clock phase, to feed current to both the sensor system and the at least one first and second contact surfaces, and to feed the first feed line and the second feed line with current during a second, complementary clock phase;

a configuration of the power cut-off element, in the current path to the sensor or in the current path to the at least one first and second contact surfaces, is such that the power cut-off element becomes active during the second clock phase corresponding to a polarity of the fed current;

during the first clock phase the contact signal as well as the sensor signal are present in the measuring current at an output of the measuring device in the form of the sum signal; and during the second clock phase only the sensor signal is present in the sum signal of the measuring current at the output of the measuring device.

18. A measuring device method comprising:

providing a medical device with at least one measuring device connected to the medical device by a feed circuit feeding current to the measuring device alternatingly via a first feed line and a second feed line, wherein the measuring device comprises:

at least one sensor connected to the first feed line and the second feed line, wherein the measuring device is positionable on skin surface of a patient for the at least one sensor to detect a measured value;

at least one first contact surface connected to the first feed line and the second feed line, the at least one first contact surface being provided on an underside of the measuring device;

at least one second contact surface connected to the first feed line and the second feed line, the at least one second contact surface being provided on the underside of the measuring device, which said underside is intended for being in electrical contact with the skin surface of the patient, the at least one first contact surface and the at least one second contact surface being arranged to have a resistance between the at least one first contact surface and the at least one second contact surface that is a function of electrical contact with the skin; and a detecting means for detecting a measuring current resulting from a particular effective electric resistance between the at least one first contact surface and second contact surface, the detected measuring current comprising a contact signal and being a function of electrical contact of the at least one first contact surface and the at least one second contact surface with the skin, wherein the sensor and the at least one first and second contact surfaces are connected electrically in parallel to the first feed line and the second feed line and wherein a power cut-off element, is located either in a current path to the sensor or in a current path to the at least one first and second contact surfaces; and feeding current to the measuring device by means of the medical device alternatingly via the first and second feed lines, and the measuring current comprising the contact signal and a sensor signal as a sum signal, which sum signal can be analyzed by means of the medical device during operation, is fed to the medical device by the measuring device via a respective complementary feed line.

19. A method in accordance with claim 18 wherein the measuring device further comprises a local power source.

* * * * *